US 7,900,505 B2

(12) United States Patent
Mutz et al.

(10) Patent No.: US 7,900,505 B2
(45) Date of Patent: *Mar. 8, 2011

(54) ACOUSTIC ASSESSMENT OF FLUIDS IN A PLURALITY OF RESERVOIRS

(75) Inventors: Mitchell W. Mutz, Palo Alto, CA (US); Richard N. Ellson, Palo Alto, CA (US); James K. Foote, Cupertino, CA (US)

(73) Assignee: Labcyte Inc., Sunnyvale, CA (US)

( * ) Notice: Subject to any disclaimer, the term of this patent is extended or adjusted under 35 U.S.C. 154(b) by 926 days.

This patent is subject to a terminal disclaimer.

(21) Appl. No.: 11/329,817

(22) Filed: Jan. 10, 2006

(65) Prior Publication Data

US 2006/0156797 A1 Jul. 20, 2006

Related U.S. Application Data

(63) Continuation-in-part of application No. 10/703,737, filed on Nov. 6, 2003, now abandoned, which is a continuation-in-part of application No. 09/964,212, filed on Sep. 25, 2001, now Pat. No. 6,666,541, which is a continuation-in-part of application No. 09/727,392, filed on Nov. 29, 2000, now abandoned, which is a continuation-in-part of application No. 09/669,996, filed on Sep. 25, 2000, now abandoned.

(51) Int. Cl.
*G01N 29/00* (2006.01)
(52) U.S. Cl. ...................................................... 73/64.53
(58) Field of Classification Search ................. 73/61.79, 73/64.53, 649
See application file for complete search history.

(56) References Cited

U.S. PATENT DOCUMENTS

| 3,608,715 A | 9/1971 | Snyder et al. ................. 209/590 |
| 4,308,547 A | 12/1981 | Lovelady et al. ............... 347/46 |
| 4,391,129 A | 7/1983 | Trinh et al. .................. 73/64.48 |
| 4,558,589 A | 12/1985 | Hemmes ...................... 73/64.42 |
| 4,901,245 A | 2/1990 | Olson et al. ..................... 702/54 |
| 5,041,849 A | 8/1991 | Quate et al. ..................... 347/46 |
| 5,056,357 A | 10/1991 | Dymling et al. ............. 73/54.41 |
| 5,255,564 A | 10/1993 | Glad et al. ....................... 73/597 |

(Continued)

FOREIGN PATENT DOCUMENTS

EP 0 294 172 12/1988

(Continued)

OTHER PUBLICATIONS

U.S. Appl. No. 09/669,194, filed Sep. 25, 2000, Ellson et al.

(Continued)

*Primary Examiner* — Hezron Williams
*Assistant Examiner* — Tamiko D Bellamy
(74) *Attorney, Agent, or Firm* — Jones Day

(57) ABSTRACT

The invention provides devices and methods for acoustically assessing the contents in a plurality of reservoirs. Each reservoir has a portion adapted to contain a fluid, and an acoustic radiation generator is positioned in acoustic coupling relationship to each of the reservoirs. Acoustic radiation generated by the acoustic radiation generator is transmitted through at least the portion of each reservoir to an analyzer. The analyzer is capable of analyzing a characteristic of the transmitted acoustic radiation and optionally correlating the characteristic to a property of the reservoirs' contents. The invention is particularly suited for assessing the contents of a plurality of reservoirs to allow for accuracy and control over the dispensing of fluids therefrom.

52 Claims, 2 Drawing Sheets

U.S. PATENT DOCUMENTS

| | | | |
|---|---|---|---|
| 5,410,518 A | 4/1995 | Birkett | 367/87 |
| 5,471,872 A | 12/1995 | Cummings | 73/290 V |
| 5,507,178 A | 4/1996 | Dam | 73/61.49 |
| 5,520,715 A | 5/1996 | Oeftering | 73/335 |
| 5,533,402 A | 7/1996 | Sarvazyan et al. | 73/675 |
| 5,594,165 A | 1/1997 | Madanshetty | 73/61.75 |
| 5,623,095 A | 4/1997 | Beller | 73/61.49 |
| 5,739,432 A | 4/1998 | Sinha | 73/579 |
| 5,767,407 A | 6/1998 | Sinha | 73/579 |
| 5,793,705 A | 8/1998 | Gazis et al. | 367/98 |
| 5,798,779 A | 8/1998 | Nakayasu et al. | 347/46 |
| 5,804,698 A | 9/1998 | Belonenko et al. | 73/1.83 |
| 5,880,364 A | 3/1999 | Dam | 73/149 |
| 5,922,945 A | 7/1999 | Allmaras et al. | 73/52 |
| 5,985,356 A | 11/1999 | Schultz et al. | 427/8 |
| 6,119,510 A | 9/2000 | Carasso et al. | 73/61.75 |
| 6,227,040 B1 | 5/2001 | Hastings et al. | 73/54.41 |
| 6,298,726 B1 | 10/2001 | Adachi et al. | 73/653 |
| 6,863,362 B2 | 3/2005 | Reichel et al. | 347/19 |
| 6,925,856 B1 | 8/2005 | Williams | 73/64.48 |
| 6,932,097 B2 * | 8/2005 | Ellson et al. | 137/2 |
| 6,938,995 B2 * | 9/2005 | Mutz et al. | 347/75 |
| 2002/0037375 A1 | 3/2002 | Ellson et al. | 427/600 |
| 2002/0037579 A1 | 3/2002 | Ellson et al. | 435/287.2 |
| 2002/0094582 A1 | 7/2002 | Williams et al. | 436/180 |
| 2002/0155231 A1 | 10/2002 | Ellson et al. | 427/600 |
| 2003/0101819 A1 * | 6/2003 | Mutz et al. | 73/602 |
| 2004/0014029 A1 | 1/2004 | Mutz et al. | 506/12 |
| 2004/0119793 A1 * | 6/2004 | Mutz et al. | 347/75 |

FOREIGN PATENT DOCUMENTS

| | | |
|---|---|---|
| EP | 0 972 564 A2 | 1/2000 |
| EP | 1208913 A2 | 5/2002 |
| EP | 1208914 A2 | 5/2002 |
| EP | 1209466 A2 | 5/2002 |
| WO | WO 95/35505 | 12/1995 |

OTHER PUBLICATIONS

Amemiya et al. (1997), "Ink Jet Printing with Focused Ultrasonic Beams," *IS&T's NIP13: 1997 International Conference on Digital Printing Technologies*, pp. 698-702.

European Search Report, dated Oct. 31, 2007, for European patent application No. 07 00 3181.0.

* cited by examiner

ACOUSTIC ASSESSMENT OF FLUIDS IN A PLURALITY OF RESERVOIRS

CROSS-REFERENCE TO RELATED APPLICATIONS

This is a continuation-in-part of U.S. patent application Ser. No. 10/703,737, filed Nov. 6, 2003, which is a continuation-in-part of application Ser. No. 09/964,212 filed Sep. 25, 2001, issued as U.S. Pat. No. 6,666,541, which is a continuation-in-part of U.S. patent application Ser. No. 09/727,392, filed Nov. 29, 2000, now abandoned, which is a continuation-in-part of U.S. patent application Ser. No. 09/669,996, filed Sep. 25, 2000, now abandoned. All the applications recited in this paragraph are incorporated by reference herein.

TECHNICAL FIELD

The invention relates generally to the use of acoustic energy to assess the contents of a plurality of reservoirs. In particular, the invention relates to devices and methods for acoustically assessing the contents of a plurality of reservoirs in order to enhance accuracy and precision in dispensing fluids from the reservoirs. The invention is particularly suited for use in conjunction with combinatorial synthetic and analytical systems that employ biomolecular libraries containing a large number of different fluid reservoirs.

BACKGROUND

The discovery of novel and useful materials depends largely on the capacity to make and characterize new compositions of matter. As a result, recent research relating to novel materials having useful biological, chemical, and/or physical properties has focused on the development and implementation of new methods and systems for synthesizing and evaluating potentially useful chemical compounds. In particular, high-speed combinatorial methods have been developed to address the general need in the art for systematic, efficient, and economical material synthesis techniques as well as for methods to analyze and to screen novel materials for useful properties.

Generally, it is important to control the quality of the starting materials in any chemical synthesis process. Otherwise, the integrity of the process and the quality of the resulting product would be compromised. Quality control of the starting materials is a particularly important issue in combinatorial synthesis procedures. In such procedures, for example, those employed in peptide drug discovery applications, a large number of starting compounds may be dispensed in a predetermined sequence from a compound library to synthesize a batch of a drug containing a specific peptide sequence. Should any of the starting compounds contain an unacceptable level of a contaminant or exhibit an unacceptable degree of degradation, the resulting compound may be rendered useless. In effect, all starting compounds employed for the batch synthesis would be wasted. This is particularly problematic when the one or more of the starting compounds are rare or expensive.

Similarly, combinatorial testing techniques may be employed in analytical and testing procedures. For example, a plurality of pharmacologically active candidate compounds may be delivered to a test sample in combination in order to assess whether synergistic effects are achieved. If any one of the candidate compounds is compromised in quality, however, the accuracy and reliability of the assessment may be reduced. Thus, further testing may be necessary, adding significantly to the overall time and cost associated with the combinatorial testing process.

High-speed combinatorial methods often involve the use of array technologies that require accurate dispensing of fluids each having a precisely known chemical composition, concentration, stoichiometry, ratio of reagents, and/or volume. Such array technologies may be employed to carry out various synthetic processes and evaluations. Array technologies may employ large numbers of different fluids to form a plurality of reservoirs that, when arranged appropriately, create combinatorial libraries. In order to carry out combinatorial techniques, a number of fluid dispensing techniques have been explored, such as pin spotting, pipetting, inkjet printing, and acoustic ejection. Many of these techniques possess inherent drawbacks that must be addressed, however, before the fluid dispensing accuracy required for the combinatorial methods can be achieved. For instance, a number of fluid dispensing systems are constructed using networks of tubing or other fluid-transporting vessels. Tubing, in particular, can entrap air bubbles, and nozzles may become clogged by lodged particulates. As a result, system failure may occur and cause spurious results. Furthermore, cross-contamination between the reservoirs of compound libraries may occur due to inadequate flushing of tubing and pipette tips between fluid transfer events. Cross-contamination can easily lead to inaccurate and misleading results.

Acoustic ejection provides a number of advantages over other fluid-dispensing technologies. In contrast to inkjet devices, nozzleless fluid ejection devices are not subject to clogging and its associated disadvantages, e.g., misdirected fluid or improperly sized droplets. Furthermore, acoustic technology does not require the use of tubing or involve invasive mechanical actions, for example, those associated with the introduction of a pipette tip into a reservoir of fluid.

Acoustic ejection has been described in a number of patents. For example, U.S. Pat. No. 4,308,547 to Lovelady et al. describes a liquid drop emitter that utilizes acoustic principles to eject droplets from a body of liquid onto a moving document to result in the formation of characters or bar codes thereon. A nozzleless inkjet printing apparatus is used in which controlled drops of ink are propelled by an acoustic force produced by a curved transducer at or below the surface of the ink. Similarly, U.S. patent application Ser. No. 09/964,212 describes a device for acoustically ejecting a plurality of fluid droplets toward discrete sites on a substrate surface for deposition thereon. The device includes an acoustic radiation generator that may be used to eject fluid droplets from a reservoir, as well as to produce an acoustic wave for detection that is transmitted to the fluid surface of the reservoir to become a reflected acoustic wave. Characteristics of the reflected acoustic radiation may then be analyzed in order to assess the spatial relationship between the acoustic radiation generator and the fluid surface. Thus, acoustic ejection may provide an added advantage in that the proper use of acoustic radiation provides feedback relating to the process of acoustic ejection itself.

Regardless of the dispensing technique used, however, inventory and materials handling limitations generally dictate the capacity of combinatorial methods to synthesize and analyze increasing numbers of sample materials. For instance, during the formatting and dispensing processes, microtiter plates that contain a plurality of fluids in individual wells may be thawed, and the contents of selected wells then extracted for use in a combinatorial method. When a pipetting system is employed during extraction, a minimum loading volume may be required for the system to function properly. Similarly, other fluid dispensing systems may also require a certain minimum reservoir volume to function properly. Thus, for any fluid dispensing system, it is important to monitor the reservoir contents to ensure that at least a minimum amount of fluid is provided. Such content monitoring generally serves to describe the overall performance of a fluid dispensing system, as well as to maintain the integrity of the combinatorial methods.

In addition, during combinatorial synthesis or analysis processes, environmental effects may play a role in altering the reservoir contents. For example, dimethylsulfoxide (DMSO) is a common organic solvent employed to dissolve or suspend compounds commonly found in drug libraries. DMSO is highly hygroscopic and tends to absorb any ambient water with which it comes into contact. The absorption of water dilutes the concentration of the compounds in the DMSO as well as altering the ability of the DMSO to suspend the compounds. Furthermore, the absorption of water may promote the decomposition of water-sensitive compounds.

A number of patents describe the use of acoustic energy to assess the contents of a container. U.S. Pat. No. 5,507,178 to Dam, for example, describes a sensor for determining the presence of a liquid and for identifying the type of liquid in a container. The ultrasonic sensor determines the presence of the liquid through an ultrasonic "liquid presence sensing means" and identifies the type of liquid through a "liquid type identification means" that includes a pair of electrodes and an electrical pulse generating means. This device suffers from the disadvantage that the sensor must be placed in contact with the liquid.

U.S. Pat. No. 5,880,364 to Dam, on the other hand, describes a non-contact ultrasonic system for measuring the volume of liquid in a plurality of containers. An ultrasonic sensor is disposed opposite the top of the containers. A narrow beam of ultrasonic radiation is transmitted from the sensor to the open top of an opposing container to be reflected from the air-liquid interface of the container back to the sensor. By using the round trip transit time of the radiation and the dimensions of the containers being measured, the volume of liquid in the container can be calculated. This device cannot be used to assess the contents of sealed containers. In addition, the device lacks precision because air is a poor conductor of acoustic energy. Thus, while this device may provide rough estimate of the volume of liquid in relatively large containers, it is unsuitable for use in providing a detailed assessment of the contents of reservoirs typically used with combinatorial techniques. In particular, this device cannot determine the position of the bottom of containers since substantially all of the emitted acoustic energy is reflected from the liquid surface and does not penetrate to the bottom. Small volume reservoirs such as microtiter plates are regular arrays of fluid containers. The location of the bottoms of the containers in such arrays can vary by a significant fraction of the nominal height of a container due to bow in the plate. Thus, detection of the position of the liquid surface only leads to significant errors in height and thus volume estimation in common containers.

Thus, there is a need in the art for improved methods and devices that are capable of monitoring the contents of a plurality of reservoirs, a capability that is particularly useful in synthetic and analytical processes to increase the robustness, efficiency, and effectiveness of the combinatorial techniques employed therein.

SUMMARY OF THE INVENTION

In a first embodiment, the invention provides a device for acoustically assessing the contents of a plurality of fluid reservoirs each comprising a solid surface, wherein a portion of each reservoir is adapted to contain a fluid. The device also includes an acoustic radiation generator with a means for positioning the generator in an acoustically coupled relationship to each reservoir, such that the acoustic radiation generated is transmitted through the solid surface and the portion of each reservoir adapted to contain a fluid. An analyzer positioned to receive the acoustic radiation is provided for analyzing a characteristic of the transmitted acoustic radiation.

Typically, the inventive device includes a single acoustic radiation generator and a plurality of removable reservoirs. In addition, the acoustic radiation generator may comprise a component common to the analyzer, such as a piezoelectric element. Optionally, the acoustic generator may represent a component of an acoustic ejector, which ejects droplets from the reservoirs. In such a case, the device may further comprise a means to focus the acoustic radiation.

The analyzer may be adapted to analyze acoustic radiation, thereby permitting determination of the fluid volume contained in each reservoir. In addition or in the alternative, the analyzer may also be adapted to analyze acoustic radiation to determine a specific property of the fluid contained in each reservoir. The specific fluid property may be, for example, viscosity, surface tension, acoustic impedance, acoustic attenuation, solid content, or impurity content.

In another embodiment, the invention relates to a method for acoustically assessing the contents of one or more fluid reservoirs. The method involves selecting a reservoir from a plurality of reservoirs each comprising a solid surface, wherein a portion of each reservoir is adapted to contain a fluid, and positioning an acoustic radiation generator in an acoustically coupled relationship to the selected reservoir. Once positioned, the acoustic radiation generator is actuated so that generated acoustic radiation is transmitted through the solid surface and through the portion of the selected reservoir adapted to contain a fluid and to an analyzer capable of analyzing a characteristic of the transmitted radiation. The analyzer is then operated to analyze the characteristic of the transmitted radiation in order to assess the contents of the selected reservoir. Optionally, the acoustic radiation generator could be repositioned to permit assessment of the contents of the remaining reservoirs.

Typically, the contents of the selected reservoir are assessed by determining the difference in the acoustic radiation before and after transmission through the reservoir. The results of the acoustic analysis may be stored electronically for later use.

In a further embodiment, the invention relates to a method for accurately dispensing fluid from one or more reservoirs. The method involves positioning an acoustic radiation generator in an acoustically coupled relationship to a reservoir selected from a plurality of reservoirs, in order to transmit acoustic radiation through at least a portion of the selected reservoir adapted to contain a fluid. A characteristic of the transmitted acoustic radiation is then analyzed in order to assess the reservoir's contents. Once the acoustic radiation characteristic has been assessed by the acoustic radiation analysis, fluid is dispensed accordingly from the selected reservoir, preferably by acoustic means.

In yet a further embodiment, the invention relates to a device for dispensing a fluid from a plurality of reservoirs each having a portion adapted to contain a fluid. Improvement in the device is accomplished by providing an acoustic radiation generator, a means for positioning the acoustic radiation generator in an acoustically coupled relationship to each reservoir such that acoustic radiation is transmitted through at least the portion of each reservoir, and an analyzer for analyzing the acoustic radiation. The analyzer is positioned to receive the transmitted acoustic radiation.

BRIEF DESCRIPTION OF THE DRAWINGS

FIG. 1A shows the acoustic ejector acoustically coupled to the first reservoir; the ejector is activated in order to eject a droplet of fluid from within the first reservoir toward a site on a substrate surface to form an array. FIG. 1B shows the acoustic ejector acoustically coupled to a second reservoir.

DETAILED DESCRIPTION OF THE INVENTION

Figure 1A:
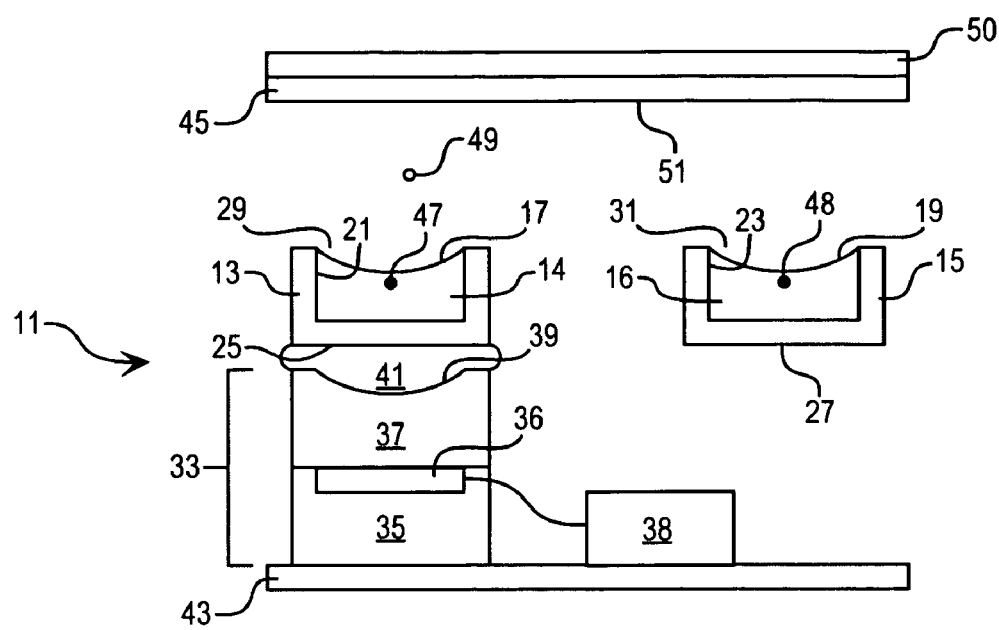
FIGS. 1A and 1B, collectively referred to as FIG. 1, schematically illustrate in simplified cross-sectional view a preferred embodiment of the invention that allows both the acoustic assessment in reflective mode of the contents of a plurality of reservoirs and the ejection of fluid droplets therefrom. As depicted, the device comprises first and second reservoirs, a combined acoustic analyzer and ejector, and an ejector positioning means.

Before describing the present invention in detail, it is to be understood that this invention is not limited to specific fluids, biomolecules, or device structures, as such may vary. It is also to be understood that the terminology used herein is for the purpose of describing particular embodiments only, and is not intended to be limiting.

It must be noted that, as used in this specification and the appended claims, the singular forms "a," "an," and "the" include plural referents unless the context clearly dictates otherwise. Thus, for example, reference to "a reservoir" includes a plurality of reservoirs, reference to "a fluid" includes a plurality of fluids, reference to "a biomolecule" includes a combination of biomolecules, and the like.

In describing and claiming the present invention, the following terminology will be used in accordance with the definitions set forth below.

The terms "acoustic coupling" and "acoustically coupled" as used herein refer to a state wherein an object is placed in direct or indirect contact with another object so as to allow acoustic radiation to be transferred between the objects without substantial loss of acoustic energy. When two entities are indirectly acoustically coupled, an "acoustic coupling medium" is needed to provide an intermediary through which acoustic radiation may be transmitted. Thus, an ejector may be acoustically coupled to a fluid, such as by immersing the ejector in the fluid, or by interposing an acoustic coupling medium between the ejector and the fluid, in order to transfer acoustic radiation generated by the ejector through the acoustic coupling medium and into the fluid.

The term "attached," as in, for example, a substrate surface having a moiety "attached" thereto, includes covalent and noncovalent binding, adsorption, and physical immobilization. The terms "binding" and "bound" are identical in meaning to the term "attached."

The term "array" as used herein refers to a two-dimensional arrangement of features, such as an arrangement of reservoirs (e.g., wells in a well plate) or an arrangement of different moieties, including ionic, metallic, or covalent crystalline, e.g., molecular crystalline, composite or ceramic, glassine, amorphous, fluidic or molecular materials on a substrate surface (as in an oligonucleotide or peptidic array). Arrays are generally comprised of regular, ordered features, as in, for example, a rectilinear grid, parallel stripes, spirals, and the like, but non-ordered arrays may be advantageously used as well. An array is distinguished from the more general term "pattern" in that patterns do not necessarily contain regular and ordered features.

The terms "biomolecule" and "biological molecule" are used interchangeably herein to refer to any organic molecule that is, was, or can be a part of a living organism, regardless of whether the molecule is naturally occurring, recombinantly produced, or chemically synthesized in whole or in part. The terms encompass, for example, nucleotides, amino acids, and monosaccharides, as well as oligomeric and polymeric species, such as oligonucleotides and polynucleotides, peptidic molecules, such as oligopeptides, polypeptides and proteins, saccharides such as disaccharides, oligosaccharides, polysaccharides, mucopolysaccharides or peptidoglycans (peptidopolysaccharides) and the like. The terms also encompass ribosomes, enzyme cofactors, pharmacologically active agents, and the like. Additional information relating to the term "biomolecule" can be found in U.S. Ser. No. 09/964,212.

The term "fluid" as used herein refers to matter that is nonsolid, or at least partially gaseous and/or liquid, but not entirely gaseous. A fluid may contain a solid that is minimally, partially, or fully solvated, dispersed, or suspended. Examples of fluids include, without limitation, aqueous liquids (including water per se and salt water) and nonaqueous liquids such as organic solvents and the like. As used herein, the term "fluid" is not synonymous with the term "ink" in that an ink must contain a colorant and may not be gaseous.

The terms "focusing means" and "acoustic focusing means" refer to a means for causing acoustic waves to converge at a focal point, either by a device separate from the acoustic energy source that acts like an optical lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased arrays as are known in the art and described, for example, in U.S. Pat. No. 5,798,779 to Nakayasu et al. and Amemiya et al. (1997) *Proceedings of the* 1997 *IS&T NIP* 13 *International Conference on Digital Printing Technologies*, pp. 698-702.

The terms "library" and "combinatorial library" are used interchangeably herein to refer to a plurality of chemical or biological moieties arranged in a pattern or an array such that the moieties are individually addressable. In some instances, the plurality of chemical or biological moieties is present on the surface of a substrate, and in other instances, the plurality of moieties represents the contents of a plurality of reservoirs. Preferably, but not necessarily, each moiety is different from each of the other moieties. The moieties may be, for example, peptidic molecules and/or oligonucleotides.

The term "moiety" refers to any particular composition of matter, e.g., a molecular fragment, an intact molecule (including a monomeric molecule, an oligomeric molecule, and a polymer), or a mixture of materials (for example, an alloy or a laminate).

"Optional" or "optionally" means that the subsequently described circumstance may or may not occur, so that the description includes instances where the circumstance occurs and instances where it does not.

The term "reservoir" as used herein refers to a receptacle or chamber for containing a fluid. In some instances, a fluid contained in a reservoir necessarily will have a free surface, e.g., a surface that allows acoustic radiation to be reflected therefrom or a surface from which a droplet may be acoustically ejected. A reservoir may also be a locus on a substrate surface within which a fluid is constrained.

The term "substrate" as used herein refers to any material having a surface onto which one or more fluids may be deposited. The substrate may be constructed in any of a number of forms including, for example, wafers, slides, well plates, or membranes. In addition, the substrate may be porous or nonporous as required for deposition of a particular fluid. Suitable substrate materials include, but are not limited to, supports that are typically used for solid phase chemical synthesis, such as polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, and divinylbenzene styrene-based polymers), agarose (e.g., Sepharose®), dextran (e.g., Sephadex®), cellulosic polymers and other polysaccharides, silica and silica-based materials, glass (particularly controlled pore glass, or "CPG"), functionalized glasses, ceramics, and such substrates treated with surface coatings, e.g., with microporous polymers (particularly cellulosic polymers such as nitrocellulose), microporous metallic compounds (particularly microporous aluminum), antibody-binding proteins (available from Pierce Chemical Co., Rockford Ill.), bisphenol A polycarbonate, or the like. Additional information relating to the term "substrate" can be found in U.S. patent application Ser. No. 09/964,212.

The invention accordingly relates to devices and methods for acoustically assessing the contents of a plurality of fluid reservoirs. An embodiment of the invention is a device which includes a plurality of reservoirs, each adapted to contain a fluid, and an acoustic radiation generator for generating acoustic radiation. The inventive device also includes a means for positioning the acoustic radiation generator in an acoustically coupled relationship to each reservoir such that the acoustic radiation generated by the acoustic radiation generator is transmitted through at least a portion of each reservoir. An analyzer for analyzing a characteristic of acoustic radiation is positioned to receive the transmitted acoustic radiation.

The device may be constructed to include the reservoirs as an integrated or permanently attached component of the device. However, to provide modularity and interchangeability of components, it is preferred that device be constructed with removable reservoirs. Generally, the reservoirs are arranged in a pattern or an array to provide each reservoir with individual systematic addressability. In addition, while each of the reservoirs may be provided as a discrete or stand-alone item, in circumstances that require a large number of reservoirs, it is preferred that the reservoirs be attached to each other or represent integrated portions of a single reservoir unit. For example, the reservoirs may represent individual wells in a well plate. Many well plates suitable for use with the device are commercially available and may contain, for example, 96, 384, 1536, or 3456 wells per well plate. Manufactures of suitable well plates for use in the employed device include Corning, Inc. (Corning, N.Y.) and Greiner America, Inc. (Lake Mary, Fla.). However, the availability of such commercially available well plates does not preclude the manufacture and use of custom-made well plates containing at least about 10,000 wells, or as many as 100,000 to 500,000 wells, or more.

Furthermore, the material used in the construction of reservoirs must be compatible with the fluids contained therein. Thus, if it is intended that the reservoirs or wells contain an organic solvent such as acetonitrile, polymers that dissolve or swell in acetonitrile would be unsuitable for use in forming the reservoirs or well plates. Similarly, reservoirs or wells intended to contain DMSO must be compatible with DMSO. For water-based fluids, a number of materials are suitable for the construction of reservoirs and include, but are not limited to, ceramics such as silicon oxide and aluminum oxide, metals such as stainless steel and platinum, and polymers such as polyester and polytetrafluoroethylene. For fluids that are photosensitive, the reservoirs may be constructed from an optically opaque material that has sufficient acoustic transparency for substantially unimpaired functioning of the device.

In addition, to reduce the amount of movement and time needed to align the acoustic radiation generator with each reservoir or reservoir well during operation, discussed infra, it is preferable that the center of each reservoir be located not more than about 1 centimeter, preferably not more than about 1 millimeter, and optimally not more than about 0.5 millimeter, from a neighboring reservoir center. These dimensions tend to limit the size of the reservoirs to a maximum volume. The reservoirs are constructed to contain typically no more than about 1 mL, preferably no more than about 1 µL, and optimally no more than about 1 nL, of fluid. To facilitate handling of multiple reservoirs, it is also preferred that the reservoirs be substantially acoustically indistinguishable.

Generally, a single acoustic radiation generator is employed, though a plurality of acoustic radiation generators may be employed as well. All acoustic radiation generators employ a vibrational element or transducer to generate acoustic radiation. Often, a piezoelectric element is employed to convert electrical energy into mechanical energy associated with acoustic radiation. When a single acoustic radiation generator is employed, the positioning means should allow for the acoustic radiation generator to move from one reservoir to another quickly and in a controlled manner, thereby allowing fast and controlled scanning of the contents of the reservoirs. In order to ensure optimal performance, it is important to keep in mind that there are two basic kinds of motion: pulse and continuous. Pulse motion involves the discrete steps of moving an acoustic radiation generator into position, keeping it stationary while it emits acoustic energy, and moving the generator to the next position; again, using a high performance positioning means with such a method allows repeatable and controlled acoustic coupling at each reservoir in less than 0.1 second. Typically, the pulse width is very short and may enable over 10 Hz reservoir transitions, and even over 1000 Hz reservoir transitions. A continuous motion design, on the other hand, moves the acoustic radiation generator and the reservoirs continuously, although not at the same speed.

In some instances, the analyzer is positioned in fixed alignment with respect to the acoustic radiation generator. In other instances, however, a means similar to that described above is provided for altering the relative positions of the analyzer with respect to the reservoirs. The relative position of the analyzer and the acoustic radiation generator depends on the particular configuration of the device. In some instances, the device may be configured to operate in transmissive mode, such that the generated radiation is transmitted through the entirety of the reservoir whose contents are assessed. In such a case, the reservoir may be interposed between the acoustic radiation generator and an acoustic analyzer. As another option, the device may be configured to operate in a reflective mode, such that the acoustic radiation is transmitted only through a portion the reservoir whose contents are being assessed. In such a case, the analyzer may be positioned in a manner appropriate for this configuration, e.g., in order to receive reflected acoustic radiation. In any case, the acoustic radiation generator should be positioned such that generated acoustic radiation is transmitted through the portion of each reservoir most likely to contain a fluid for optimal performance. This reduces the chance that the analyzer will erroneously determine that a reservoir is empty. For example, as fluids ordinarily flow to the bottom of containers or are driven there by centrifugation; the acoustic radiation generator should be positioned such that generated acoustic radiation can be transmitted through the bottom of a reservoir.

In a preferred configuration, as discussed in detail below, the analyzer is positioned to receive acoustic radiation reflected from a free surface of a fluid contained in each reservoir. In such a configuration, the acoustic radiation generator may comprise one or more components shared with the analyzer. The components common to the acoustic radiation generator and the analyzer may include a vibrational element that converts one form of energy into another, e.g., a piezoelectric element that converts between acoustic/mechanical energy and electrical energy.

The analyzer may be constructed to perform a number of functions. For example, the analyzer may be adapted to analyze acoustic radiation to determine the volume of fluid in each reservoir. In addition, or in the alterative, the analyzer may be adapted to analyze acoustic radiation to determine a property of fluid in each reservoir. Fluid properties that can be determined in this manner include, but are not limited to, viscosity, surface tension, acoustic impedance, acoustic attenuation, solid content, and impurity content.

Thus, the invention also provides a method for acoustically assessing the contents of one or more reservoirs. The method involves providing a plurality of reservoirs, each reservoir adapted to contain a fluid, and positioning an acoustic radiation generator in acoustic coupling relationship to a selected reservoir. Once positioned, the acoustic radiation generator is actuated to generate acoustic radiation that is transmitted through at least a portion of the selected reservoir to an analyzer. The analyzer is then used to analyze acoustic radiation that has been transmitted through at least a portion of the selected reservoir, thereby assessing the contents of the selected reservoir. Optionally, the acoustic radiation generator may be repositioned to allow for the assessment of the contents of the remaining reservoirs as well.

As discussed above, the reservoirs may be constructed to reduce the amount of movement and time needed to align the acoustic radiation generator with each reservoir or reservoir well during operation. As a general matter of convenience and efficiency, it is desirable to analyze an entire library of different moieties in a relatively short amount of time, e.g., about one minute. Thus, the inventive method typically allows for the analysis of the contents of the reservoirs at a rate of at least about 96 reservoirs per minute. Faster analysis rates of at least about 384, 1536, and 3456 reservoirs per minute are achievable with present-day technology as well. Thus, the invention can be operated to analyze in one minute the contents of each well of most (if not all) well plates that are currently commercially available. Proper implementation of the inventive method should yield a reservoir analysis rate of at least about 10,000 reservoirs per minute. Current commercially available positioning technology allows the acoustic radiation generator to be moved from one reservoir to another, with repeatable and controlled acoustic coupling at each reservoir, in less than about 0.1 second for high performance positioning means and in less than about 1 second for ordinary positioning means. A custom designed system will allow the acoustic radiation generator to be moved from one reservoir to another with repeatable and controlled acoustic coupling in less than about 0.001 second.

By analyzing acoustic radiation that has been transmitted through at least a portion of a selected reservoir, one may accurately determine the contents of the selected reservoir. For example, the assessment may involve determining the volume of fluid in the reservoir or determining a property of the fluid in the reservoir. As discussed above, fluid properties that may be determined include, but are not limited to, viscosity, surface tension, acoustic impedance, solid content, and impurity content. In some instances, the assessment may involve measuring the travel time of acoustic radiation through the reservoir. In addition, or in the alternative, the assessment may involve determining the difference of acoustic radiation before and after transmission through the reservoir. For temperature-dependent properties, a temperature measurement means known in art, such as thermocouples, may be used in conjunction with such analyses. Optionally, the results of acoustic analysis performed by the acoustic analyzer may be stored. Thus, the inventive device may include, for example, a storage means comprising rewritable and/or permanent data storage media for storing the results of acoustic analysis performed by the analyzer.

Acoustic assessment as described above may be employed to improve fluid dispensing from each of a plurality of reservoirs adapted to contain a fluid. Thus, another embodiment of the invention relates to a device for dispensing fluid from each of a plurality of reservoirs adapted to contain a fluid. This device may include any of a number of known techniques for dispensing fluids involving contact-based fluid dispensing, e.g., pin spotting, pipetting, and inkjet printing, or non-contact based fluid dispensing, e.g., acoustic ejection. However, the inventive device represents a novel and nonobvious improvement over the fluid dispensing devices known in the art since it provides for enhanced accuracy and precision in fluid dispensing through the use of a means for acoustically assessing the contents of the reservoirs. The means for acoustically assessing the contents of the reservoirs is similar to the previously described device for assessing the contents of a plurality of fluid reservoirs in that it also comprises an acoustic radiation generator for generating acoustic radiation and an analyzer for analyzing a characteristic of acoustic radiation. A means for positioning the acoustic radiation generator in acoustic coupling relationship to each reservoir is used to ensure that acoustic radiation generated by the acoustic radiation generator is transmitted through at least a portion of each reservoir. Furthermore, the analyzer is positioned to receive the transmitted acoustic radiation.

As discussed above, acoustic ejection provides a number of advantages over other fluid dispensing technologies. In addition, compatible acoustic ejection technology described in U.S. Ser. No. 09/964,212 involves an ejector comprising an acoustic radiation generator for generating acoustic radiation and a focusing means for focusing the acoustic radiation generated at a focal point within and sufficiently near the fluid surface in each of a plurality of reservoirs to result in the ejection of droplets therefrom. Thus, the invention also provides a device that can carry out both acoustic ejection and assessment. In such a case, the acoustic radiation generator may serve as a component of both an acoustic ejector and an acoustic assessing means.

Optionally, a focusing means is typically provided for focusing the acoustic radiation generated by the acoustic generator. In the present invention, any of a variety of focusing means may be employed in conjunction with the acoustic generator in order to eject droplets from a reservoir through the use of focused acoustic radiation. For example, one or more curved surfaces may be used to direct acoustic radiation to a focal point near a fluid surface. One such technique is described in U.S. Pat. No. 4,308,547 to Lovelady et al. Focusing means with a curved surface have been incorporated into the construction of commercially available acoustic transducers such as those manufactured by Panametrics Inc. (Waltham, Mass.). In addition, Fresnel lenses are known in the art for directing acoustic energy at a predetermined focal distance from an object plane. See, e.g., U.S. Pat. No. 5,041,849 to Quate et al. Fresnel lenses may have a radial phase profile that diffracts a substantial portion of acoustic energy into a predetermined diffraction order at diffraction angles that vary radially with respect to the lens. The diffraction angles should be selected to focus the acoustic energy within the diffraction order on a desired object plane. Optimally, the device is adapted to eject fluid from a reservoir according to the results of acoustic analysis performed by the analyzer.

The device may also provide certain performance-enhancing functionalities. For example, the device may include a means for controlling the temperature of one or more of the reservoirs. Such temperature controlling means may be employed in the inventive device to improve the accuracy of measurement and may be employed regardless of whether the device includes a fluid dispensing functionality. In the case of aqueous fluids, the temperature controlling means should have the capacity to maintain the reservoirs at a temperature above about 0° C. In addition, the temperature controlling means may be adapted to lower the temperature in the reservoirs. Such temperature lowering may be required because repeated application of acoustic energy to a reservoir of fluid may result in heating of the fluid. Such heating can result in unwanted changes in fluid properties such as viscosity, surface tension and density. Design and construction of such temperature controlling means are known to one of ordinary skill in the art and may comprise, e.g., components such a heating element, a cooling element, or a combination thereof. For many biomolecular applications, reservoirs of fluids are stored frozen and thawed for use. During use, it is generally desired that the fluid containing the biomolecule be kept at a constant temperature, with deviations of no more than about 1° C. or 2° C. therefrom. In addition, for a biomolecular fluid that is particularly heat sensitive, it is preferred that the fluid be kept at a temperature that does not exceed about 10° C. above the melting point of the fluid, preferably at a temperature that does not exceed about 5° C. above the melting point of the fluid. Thus, for example, when the biomolecule-containing fluid is aqueous, it may be optimal to keep the fluid at about 4° C. during ejection.

Moreover, the device may be adapted to assess and/or dispense fluids of virtually any type and amount desired. The fluid may be aqueous and/or nonaqueous. Examples of fluids include, but are not limited to, aqueous fluids including water per se and water-solvated ionic and non-ionic solutions, organic solvents, lipidic liquids, suspensions of immiscible fluids, and suspensions or slurries of solids in liquids. Because the invention is readily adapted for use with high temperatures, fluids such as liquid metals, ceramic materials, and glasses may be used; see, e.g., co-pending patent application U.S. Ser. No. 09/669/194 ("Method and Apparatus for Generating Droplets of Immiscible Fluids"), inventors Ellson and Mutz, filed on Sep. 25, 2000, and assigned to Picoliter, Inc. (Sunnyvale, Calif.). Furthermore, because of the precision that is possible using the inventive technology, the device may be used to eject droplets from a reservoir adapted to contain no more than about 100 nanoliters of fluid, preferably no more than 10 nanoliters of fluid. In certain cases, the ejector may be adapted to eject a droplet from a reservoir adapted to contain about 1 to about 100 nanoliters of fluid. This is particularly useful when the fluid to be ejected contains rare or expensive biomolecules, wherein it may be desirable to eject droplets having a volume of about 1 picoliter or less, e.g., having a volume in the range of about 0.025 pL to about 1 pL.

Thus, another embodiment of the invention relates to a method for dispensing fluid from one or more reservoirs. Once an acoustic radiation generator is positioned, in acoustic coupling relation to a reservoir selected from a plurality of reservoirs, acoustic radiation generated by the acoustic radiation generator may be transmitted through at least a portion of the selected reservoir. The acoustic radiation is then analyzed in order to assess the contents of the reservoir, and fluid is dispensed from the selected reservoir according to the assessment. Typically, the fluid is dispensed through acoustic ejection, though the inventive method may employ contact-based fluid dispensing either as an alternative to or as a supplement to noncontact-based fluid dispensing. Optionally, the above process may be repeated for additional reservoirs.

It should be noted that there are a number of different ways to combine acoustic assessment with fluid dispensing, depending on the intended purpose of the combination. As discussed above, fluid may be dispensed from a reservoir after the contents of the reservoir are acoustically assessed. This allows an operator to fine tune the dispensing according to the condition of the contents of the reservoir. In addition, fluid may be dispensed from a reservoir before the contents of the reservoir are acoustically assessed. In such a case, acoustic assessment may serve to confirm the quality of fluid dispensation as well as to ensure that the dispensing process does not unexpectedly alter the contents of the reservoir. For example, by assessing the volume of fluid remaining in a reservoir after a fluid has been dispensed from the reservoir, an operator may determine the quantity of fluid actually removed from the reservoir. In some instances, acoustic assessment and fluid dispensation may occur simultaneously.

FIG. 1 illustrates a preferred embodiment of the inventive device in simplified cross-sectional view. In this embodiment, the inventive device allows for acoustic assessment of the contents of a plurality of reservoirs as well as acoustic ejection of fluid droplets from the reservoirs. The inventive device is shown in operation to form a biomolecular array bound to a substrate. As with all figures referenced herein, in which like parts are referenced by like numerals, FIG. 1 is not to scale, and certain dimensions may be exaggerated for clarity of presentation. The device 11 includes a plurality of reservoirs, i.e., at least two reservoirs, with a first reservoir indicated at 13 and a second reservoir indicated at 15. Each is adapted to contain a fluid having a fluid surface. As shown, the first reservoir 13 contains a first fluid 14 and the second reservoir 15 contains a second fluid 16. Fluids 14 and 16 each have a fluid surface respectively indicated at 17 and 19. Fluids 14 and 16 may the same or different. As shown, the reservoirs are of substantially identical construction so as to be substantially acoustically indistinguishable, but identical construction is not a requirement. The reservoirs are shown as separate removable components but may, as discussed above, be fixed within a plate or other substrate. For example, the plurality of reservoirs may comprise individual wells in a well plate, optimally although not necessarily arranged in an array. Each of the reservoirs 13 and 15 is preferably axially symmetric as shown, having vertical walls 21 and 23 extending upward from circular reservoir bases 25 and 27 and terminating at openings 29 and 31, respectively, although other reservoir shapes may be used. The material and thickness of each reservoir base should be such that acoustic radiation may be transmitted therethrough and into the fluid contained within the reservoirs.

The device also includes an acoustic ejector 33 comprised of an acoustic radiation generator 35 for generating acoustic radiation and a focusing means 37 for focusing the acoustic radiation at a focal point within the fluid from which a droplet is to be ejected, near the fluid surface. The acoustic radiation generator contains a transducer 36, e.g., a piezoelectric element, commonly shared by an analyzer. As shown, a combination unit 38 is provided that both serves as a controller and a component of an analyzer. Operating as a controller, the combination unit 38 provides the piezoelectric element 36 with electrical energy that is converted into mechanical and acoustic energy. Operating as a component of an analyzer, the combination unit receives and analyzes electrical signals from the transducer. The electrical signals are produced as a result of the absorption and conversion of mechanical and acoustic energy by the transducer.

As shown in FIG. 1, the focusing means 37 may comprise a single solid piece having a concave surface 39 for focusing acoustic radiation, but the focusing means may be constructed in other ways as discussed below. The acoustic ejector 33 is thus adapted to generate and focus acoustic radiation so as to eject a droplet of fluid from each of the fluid surfaces 17 and 19 when acoustically coupled to reservoirs 13 and 15, and thus to fluids 14 and 16, respectively. The acoustic radiation generator 35 and the focusing means 37 may function as a single unit controlled by a single controller, or they may be independently controlled, depending on the desired performance of the device. Typically, single-ejector designs are preferred over multiple-ejector designs because accuracy of droplet placement and consistency in droplet size and velocity are more easily achieved with a single ejector.

There are also a number of ways to acoustically couple the ejector 33 to each individual reservoir and thus to the fluid therein. One such approach is through direct contact as is described, for example, in U.S. Pat. No. 4,308,547 to Lovelady et al., wherein a focusing means constructed from a hemispherical crystal having segmented electrodes is submerged in a liquid to be ejected. The aforementioned patent further discloses that the focusing means may be positioned at or below the surface of the liquid. However, this approach for acoustically coupling the focusing means to a fluid is undesirable when the ejector is used to eject different fluids in a plurality of containers or reservoirs, as repeated cleaning of the focusing means would be required in order to avoid cross-contamination. The cleaning process would necessarily lengthen the transition time between each droplet ejection event. In addition, in such a method, fluid would adhere to the ejector as it is removed from each container, wasting material that may be costly or rare.

Thus, a preferred approach would be to acoustically couple the ejector to the reservoirs and reservoir fluids without contacting any portion of the ejector, e.g., the focusing means, with any of the fluids to be ejected. To this end, the present invention provides an ejector positioning means for positioning the ejector in controlled and repeatable acoustic coupling with each of the fluids in the reservoirs to eject droplets therefrom without submerging the ejector therein. This typically involves direct or indirect contact between the ejector and the external surface of each reservoir. When direct contact is used in order to acoustically couple the ejector to each reservoir, it is preferred that the direct contact is wholly conformal to ensure efficient acoustic energy transfer. That is, the ejector and the reservoir should have corresponding surfaces adapted for mating contact. Thus, if acoustic coupling is achieved between the ejector and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs having a specially formed inverse surface.

Optimally, acoustic coupling is achieved between the ejector and each of the reservoirs through indirect contact, as illustrated in FIG. 1A. In this figure, an acoustic coupling medium 41 is placed between the ejector 33 and the base 25 of reservoir 13, with the ejector and reservoir located at a predetermined distance from each other. The acoustic coupling medium may be an acoustic coupling fluid, preferably an acoustically homogeneous material in conformal contact with both the acoustic focusing means 37 and each reservoir. In addition, it is preferable to ensure that the fluid medium is substantially free of material having different acoustic properties than the fluid medium itself. Furthermore, it is preferred that the acoustic coupling medium is comprised of a material having acoustic properties that facilitate the transmission of acoustic radiation without significant attenuation in acoustic pressure and intensity. Also, the acoustic impedance of the coupling medium should facilitate the transfer of energy from the coupling medium into the container. As shown, the first reservoir 13 is acoustically coupled to the acoustic focusing means 37, such that an acoustic wave is generated by the acoustic radiation generator and directed by the focusing means 37 into the acoustic coupling medium 41, which then transmits the acoustic radiation into the reservoir 13.

In operation, reservoirs 13 and 15 are each filled with first and second fluids 14 and 16, respectively, as shown in FIG. 1. The acoustic ejector 33 is positionable by means of ejector positioning means 43, shown below reservoir 13, in order to achieve acoustic coupling between the ejector and the reservoir through acoustic coupling medium 41. Once the ejector, the reservoir, and the substrate are in proper alignment, the acoustic radiation generator 35 is activated to produce acoustic radiation that is directed toward a free fluid surface 17 of the first reservoir. The acoustic radiation will then travel in a generally upward direction toward the free fluid surface 17. The acoustic radiation will be reflected under different circumstances. Typically, reflection will occur when there is a change in the acoustic property of the medium through which the acoustic radiation is transmitted. It has been observed that a portion of the acoustic radiation traveling upward will be reflected from by the reservoir bases 25 and 27 as well as the free surfaces 17 and 19 of the fluids contained in the reservoirs 13 and 15.

As discussed above, acoustic radiation may be employed for use as an analytical tool as well as to eject droplets from a reservoir. In an analytical mode, the acoustic radiation generator is typically activated so as to generate low energy acoustic radiation that is insufficiently energetic to eject a droplet from the fluid surface. This is typically done by using a short pulse (on the order of tens of nanoseconds), which is extremely short compared to that required for droplet ejection (on the order of microseconds). By determining the time it takes for the acoustic radiation to be reflected by the fluid surface back to the acoustic radiation generator, and then correlating that time with the speed of sound in the fluid, the distance—and thus the fluid height—may be calculated. Of course, care must be taken in order to ensure that acoustic radiation reflected by the interface between the reservoir base and the fluid is discounted.

Thus, the present invention represents a significant improvement over known technologies relating to the acoustic assessment of the contents of a plurality of reservoirs. As discussed above, prior acoustic assessment of the contents of liquid reservoirs typically involved placing a sensor in direct contact with the liquid. This means that the sensor must be cleaned between each use to avoid cross-contamination of the contents of the reservoirs. In contrast, the invention allows for assessment of the contents of a plurality of containers without direct contact with the contents of the containers.

While other non-contact acoustic systems are known in the art, such systems provide only an indirect and approximate assessment of the contents of a reservoir. For example, the acoustic system described in U.S. Pat. No. 5,880,364 to Dam employs a technique in which the acoustic radiation is transmitted from a sensor through an air-containing portion of the container and then reflected from the air-liquid interface of the container back to the sensor. The round trip transit time is used to determine the volume of the air-containing portion of the container. The volume of liquid in the container is determined by subtracting the volume of the container not occupied by the liquid from the volume of the entire container. One drawback of this technique is that it cannot provide an accurate assessment of the liquid volume in a container when the volume of the container is not precisely known. This is particularly problematic when small reservoirs such as those typically used in combinatorial techniques are employed. The dimensional variability for such containers is relatively large when considered in view of the small volume of the reservoirs. Furthermore, the technique cannot be employed when the volume of the container is completely unknown or alterable. Finally, since acoustic radiation never penetrates the liquid, the reflected radiation can at best only provide information relating to the surface of the liquid, not information relating to the bulk of the liquid.

In contrast, because the invention involves the transmission of acoustic radiation through the portion of each reservoir adapted to contain a fluid, the transmitted acoustic radiation may provide information relating to the volume as well as the properties of the fluids in the reservoir. For example, the invention provides a plurality of reservoirs, wherein a portion of each reservoir is adapted to contain a fluid. A fluid contained in a reservoir must ordinarily contact a solid surface of the reservoir. When the invention is employed in a reflective mode, some of the generated acoustic radiation may be reflected by interface between the fluid and the solid surface, while the remainder is transmitted through a fluid contained in the reservoir. The transmitted radiation is then reflected by another surface, e.g., a free surface, of the fluid contained in the reservoir. By determining the difference in round-trip transit time between the two portions, the volume of the fluid in the reservoir may be accurately determined. In addition, transmission of acoustic radiation through the fluid allows characteristics of the acoustic radiation to be altered by fluid. Thus, information relating to a property of the fluid may be deduced by analyzing a characteristic of the transmitted acoustic radiation.

In addition, air, like other gases, exhibits low acoustic impedance, and acoustic radiation tends to attenuate more in gaseous materials than in liquid or solid materials. For example, the attenuation at 1 MHz for air is approximately 10 dB/cm while that of water is 0.002 dB/cm. Since the acoustic system described in U.S. Pat. No. 5,880,364 to Dam requires acoustic radiation to travel through air, this system requires much more energy to operate. Thus, the present invention represents a more energy efficient technology that may be employed to provide more accurate and detailed assessment of the contents of a plurality of fluid reservoirs. Some of this additional accuracy can be achieved by using higher frequency acoustic waves (and hence shorter wavelengths) as these acoustic waves can be transmitted effectively through liquids yet would be very rapidly attenuated in air.

It will be appreciated by those of ordinary skill in the art that conventional or modified sonar techniques may be employed. Thus, the acoustic radiation will be reflected back at the piezoelectric element 36, where the acoustic energy will be converted into electrical energy for analysis. The analysis may be used, for example, to reveal whether the reservoir contains any fluid at all. If fluid is present in the reservoir, the location and the orientation of the free fluid surface within the reservoir may be determined, as well as the overall volume of the fluid. Characteristics of the reflected acoustic radiation may be analyzed in order to assess the spatial relationship between the acoustic radiation generator and the fluid surface, the spatial relationship between a solid surface of the reservoir and the fluid surface, as well as to determine a property of the fluid in each reservoir, e.g., viscosity, surface tension, acoustic impedance, acoustic attenuation, solid content, and impurity content. Once the analysis has been performed, a decision may be made as to whether and/or how to dispense fluid from the reservoir.

Depending on the type of assessment to be carried out, various techniques known in the art may be adapted for use in the present invention. Generally, interfacial energy measurements are routinely carried out using contact-angle measurement. The present invention may be adapted to perform such contact-angle measurements. In addition, a number of other acoustic assessment techniques are known in the art. For example, U.S. Pat. No. 4,391,129 to Trinh described a system for monitoring the physical characteristics of fluids. The physical characteristic may be determined from acoustic assessment of the interfacial tension of fluids to a high degree of accuracy. U.S. Pat. No. 4,558,589 to Hemmes describes an ultrasonic blood-coagulation monitor. U.S. Pat. No. 5,056,357 to Dymling et al. described acoustic methods for measuring properties in fluids through Doppler shifts. Other acoustic assessment techniques that may be adapted for use in the present invention are described, for example, in U.S. Pat. Nos. 4,901,245, 5,255,564, 5,410,518, 5,471,872, 5,533,402, 5,594,165, 5,623,095, 5,739,432, 5,767,407, 5,793,705, 5,804,698, 6,119,510, 6,227,040, and 6,298,726.

In order to form a biomolecular array on a substrate using the inventive device, substrate 45 is positioned above and in proximity to the first reservoir 13 such that one surface of the substrate, shown in FIG. 1 as underside surface 51, faces the reservoir and is substantially parallel to the surface 17 of the fluid 14 therein. Once the ejector, the reservoir, and the substrate are in proper alignment, the acoustic radiation generator 35 is activated to produce acoustic radiation that is directed by the focusing means 37 to a focal point 47 near the fluid surface 17 of the first reservoir. That is, an ejection acoustic wave having a focal point near the fluid surface is generated in order to eject at least one droplet of the fluid, wherein the optimum intensity and directionality of the ejection acoustic wave is determined using the aforementioned analysis, optionally in combination with additional data. The "optimum" intensity and directionality are generally selected to produce droplets of consistent size and velocity. For example, the desired intensity and directionality of the ejection acoustic wave may be determined by using the data from the above-described assessment relating to reservoir volume or fluid property data, as well as geometric data associated with the reservoir. In addition, the data may show the need to reposition the ejector so as to reposition the acoustic radiation generator with respect to the fluid surface, in order to ensure that the focal point of the ejection acoustic wave is near the fluid surface, where desired. For example, if analysis reveals that the acoustic radiation generator is positioned such that the ejection acoustic wave cannot be focused near the fluid surface, the acoustic radiation generator is repositioned using vertical, horizontal, and/or rotational movement to allow appropriate focusing of the ejection acoustic wave.

As a result, droplet 49 is ejected from the fluid surface 17 onto a designated site on the underside surface 51 of the substrate. The ejected droplet may be retained on the substrate surface by solidifying thereon after contact; in such an embodiment, it may be necessary to maintain the substrate at a low temperature, i.e., a temperature that results in droplet solidification after contact. Alternatively, or in addition, a molecular moiety within the droplet attaches to the substrate surface after contract, through adsorption, physical immobilization, or covalent binding.

Figure 1B:
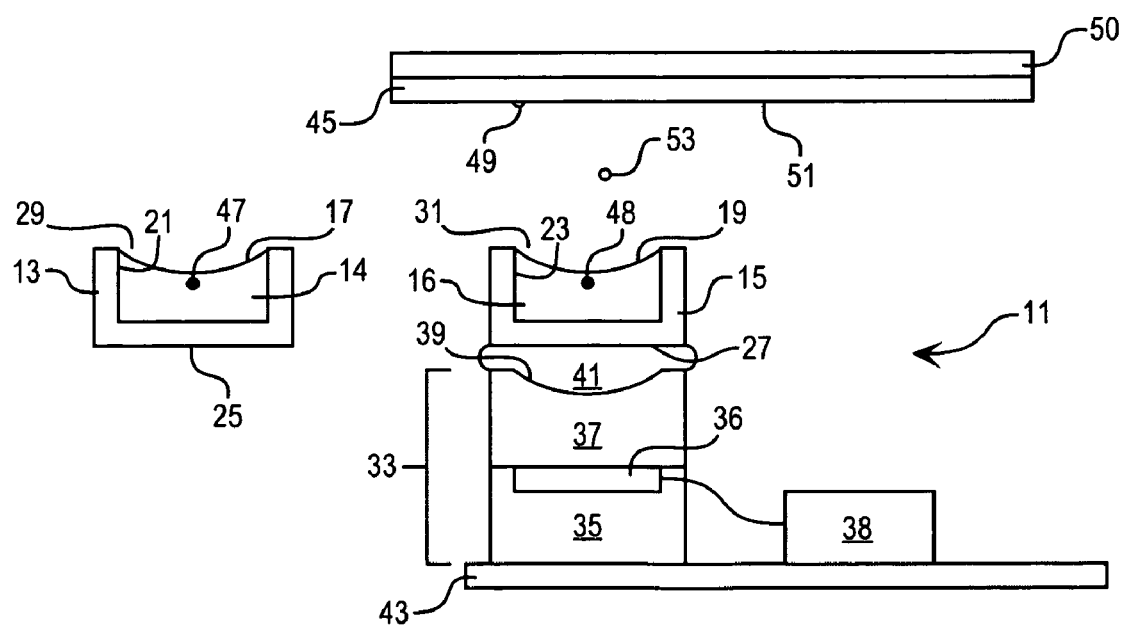

Then, as shown in FIG. 1B, a substrate positioning means 50 repositions the substrate 45 over reservoir 15 in order to receive a droplet therefrom at a second designated site. FIG. 1B also shows that the ejector 33 has been repositioned by the ejector positioning means 43 below reservoir 15 and in acoustically coupled relationship thereto by virtue of acoustic coupling medium 41. Once properly aligned, the acoustic radiation generator 35 of ejector 33 is activated to produce low energy acoustic radiation to assess the contents of the reservoir 15 and to determine whether and/or how to eject fluid from the reservoir. Historical droplet ejection data associated with the ejection sequence may be employed as well. Again, there may be a need to reposition the ejector so as to reposition the acoustic radiation generator with respect to the fluid surface, in order to ensure that the focal point of the ejection acoustic wave is near the fluid surface, where desired. Should the results of the assessment indicate that fluid may be dispensed from the reservoir, focusing means 37 is employed to direct higher energy acoustic radiation to a focal point 48 within fluid 16 near the fluid surface 19, thereby ejecting droplet 53 onto the substrate 45.

It will be appreciated that various components of the device may require individual control or synchronization to form an array on a substrate. For example, the ejector positioning means may be adapted to eject droplets from each reservoir in a predetermined sequence associated with an array to be prepared on a substrate surface. Similarly, the substrate positioning means for positioning the substrate surface with respect to the ejector may be adapted to position the substrate surface to receive droplets in a pattern or array thereon. Either or both positioning means, i.e., the ejector positioning means and the substrate positioning means, may be constructed from, for example, motors, levers, pulleys, gears, a combination thereof, or other electromechanical or mechanical means known to one of ordinary skill in the art. It is preferable to ensure that there is a correspondence between the movement of the substrate, the movement of the ejector, and the activation of the ejector to ensure proper array formation.

Accordingly, the invention relates to the assessment of the contents of a plurality of reservoirs as well as to dispensing a plurality of fluids from reservoirs, e.g., in order to form a pattern or an array, on the substrate surface 51. However, there are a number of different ways in which content assessment and fluid dispensing may relate to each other. That is, a number of different sequences may be employed for assessing the contents of the reservoirs and for dispensing fluids therefrom. In some instances, the contents of a plurality of reservoirs may be assessed before fluid is dispensed from any of the reservoirs. In other instances, the contents of each reservoir may be assessed immediately before fluid is dispensed therefrom. The sequence used typically depends on the particular fluid-dispensing technique employed as well as the intended purpose of the sequence.

Figure 2:
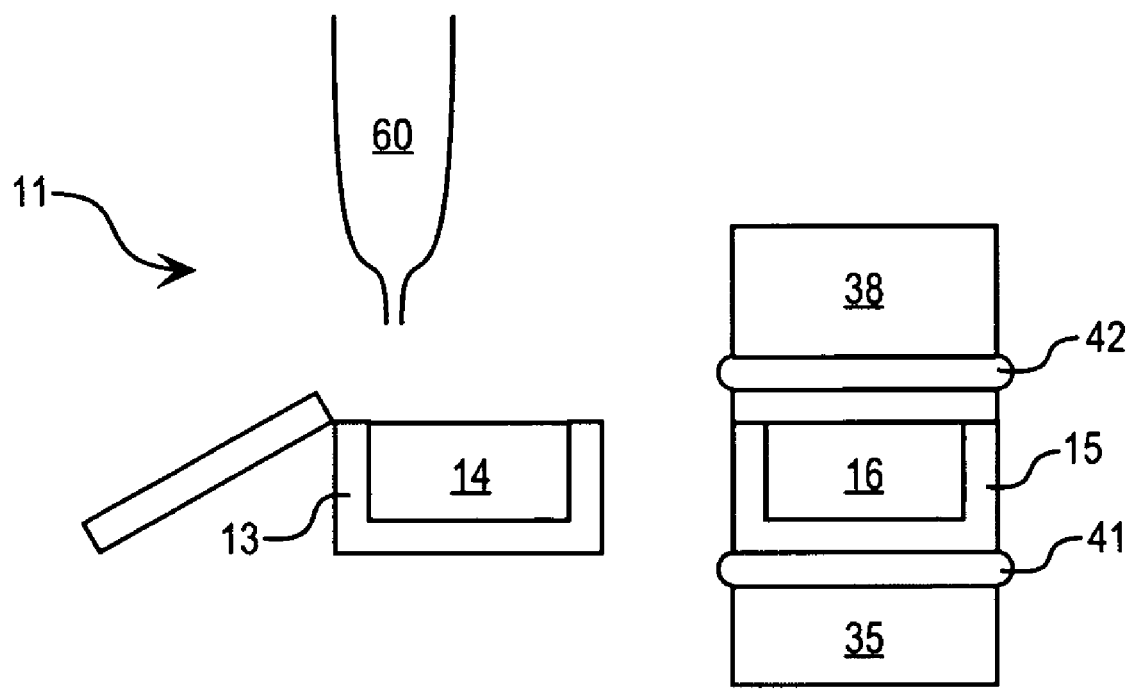
FIG. 2 schematically illustrates in simplified cross-sectional view an embodiment of the inventive device designed to permit acoustical assessment of the contents of a plurality of reservoirs in transmissive mode.

FIG. 2 illustrates an example of the inventive device that provides for assessment of the contents of a plurality of reservoirs in transmissive mode rather than in reflective mode. Considerations for the design and construction of this device are similar to those discussed above. Thus, the device 11 includes a first reservoir 13 and a second reservoir 15, each adapted to contain a fluid indicated at 14 and 16, respectively, and each of substantially identical construction. The first reservoir 13 is depicted in an open state, while the second reservoir is depicted in a sealed state. An acoustic radiation generator 35 is positioned below the reservoirs, and analyzer 38 is positioned in opposing relationship with the acoustic radiation generator 35 above the reservoirs.

In operation, the contents of each of the reservoirs are acoustically evaluated before pipette 60 is employed to dispense fluid therefrom. As shown, the contents 14 of the first reservoir 13 have already been acoustically assessed. As the assessment has revealed that the first reservoir 13 contains at least a minimum acceptable level of fluid 14, the first reservoir 13 is open and ready for fluid to be dispensed therefrom via pipette 60. The contents 16 of the second reservoir 15 are undergoing acoustic assessment, as depicted by FIG. 2, as the second reservoir 15 is interposed between the acoustic radiation generator 35 and the analyzer 38. The acoustic radiation generator 35 and the analyzer 38 are acoustically coupled to the second reservoir via coupling media 41 and 42, respectively. Once the acoustic radiation generator 35, the second reservoir 15, and the analyzer 38 are in proper alignment, the acoustic radiation generator 35 is activated to produce acoustic radiation that is transmitted through the reservoir 15 and its contents 16 toward the analyzer 38. The received acoustic radiation is analyzed by an analyzer 38 as described above It should be evident, then, that the invention provides a number of previously unrealized advantages for assessing the contents of a plurality of reservoirs. First, acoustic assessment is a generally noninvasive technique that may be carried out regardless of whether the reservoirs are sealed or open. That is, acoustic assessment does not require extracting a sample for analysis or other mechanical contact that may result in sample cross-contamination. In addition, unlike optical detection techniques, optically translucent or transparent reservoirs are not required. This, of course, provides a wider range of choices for material that may be employed for reservoir construction. In addition, the use of opaque material would be particularly advantageous in instances wherein the reservoirs are constructed to contain photosensitive fluids.

Thus, variations of the present invention will be apparent to those of ordinary skill in the art. For example, while FIG. 1 depicts the inventive device in operation to form a biomolecular array bound to a substrate, the device may be operated in a similar manner to format a plurality of fluids, e.g., to transfer fluids from odd-sized bulk containers to wells of a standardized well plate. Similarly, while FIG. 2 illustrates that the acoustic radiation generator and the detector are in vertical opposing relationship, other spatial and/or geometric arrangements may be employed so long as acoustic radiation generated is transmitted through at least a portion of the reservoir to the detector.

As another example, the invention may be employed to detect whether the contents of a sealed reservoir are at least partially frozen without opening the reservoir. This would be useful when it is known that a reservoir contains a substance that is capable of existing as a fluid over a temperature range, but it is unclear what the temperature history of the reservoir has been, e.g., whether it has been subjected to freeze-thaw cycles. For example, water is capable of existing as a fluid at a temperature of about 0° C. to about 100° C. If it is unclear whether the exterior temperature of a reservoir is indicative of the reservoir's interior temperature, but the reservoir is known to contain liquid water, the inventive device is well suited to determine whether any or all of the contents of the reservoir is a fluid.

In addition, the invention may be constructed as to be highly compatible with existing infrastructure of materials discovery and with existing automation systems for materials handling. For example, the invention may be adapted for use as an alternative or a supplement to content assessment means that are based on optical detection. In some instances, sonic markers may be provided in the reservoirs to identify the contents of the reservoir. Thus, the invention may be employed as a means for inventory identification and control in a number of contexts, including, but not limited, to biological, biochemical, and chemical discovery and analysis.

It is to be understood that while the invention has been described in conjunction with the preferred specific embodiments thereof, the foregoing description is intended to illustrate and not limit the scope of the invention. Other aspects, advantages, and modifications will be apparent to those skilled in the art to which the invention pertains.

All patents, patent applications, journal articles, and other references cited herein are incorporated by reference in their entireties.

We claim:

1. A device for acoustically determining a property of the contents of a plurality of fluid reservoirs, comprising:
    a plurality of reservoirs each comprising a solid surface, wherein a portion of each reservoir is adapted to contain a fluid;
    an acoustic radiation generator for generating acoustic radiation;
    a means for positioning the acoustic radiation generator in acoustic coupling relationship to each reservoir such that acoustic radiation generated by the acoustic radiation generator is transmitted through the solid surface and the portion of each reservoir adapted to contain a fluid; and
    an analyzer for analyzing a characteristic of the transmitted acoustic radiation.

2. The device of claim 1, comprised of a single acoustic radiation generator.

3. The device of claim 1, wherein the plurality of reservoirs are removable from the device.

4. The device of claim 1, wherein the plurality of reservoirs are individual wells in a well plate.

5. The device of claim 1, wherein the plurality of reservoirs are substantially acoustically indistinguishable.

6. The device of claim 1, wherein the plurality of reservoirs are sealed.

7. The device of claim 1, wherein the device comprises 96 reservoirs.

8. The device of claim 7, wherein the device comprises 384 reservoirs.

9. The device of claim 8, wherein the device comprises 1536 reservoirs.

10. The device of claim 9, wherein the device comprises 10,000 reservoirs.

11. The device of claim 10, wherein the device comprises 100,000 reservoirs.

12. The device of claim 1, wherein at least one reservoir is constructed to contain no more than about 100 nL of fluid.

13. The device of claim 12, wherein at least one reservoir is constructed to contain no more than about 10 nL of fluid.

14. The device of claim 1, wherein at least one reservoir contains a fluid.

15. The device of claim 14, wherein the at least one reservoir contains an aqueous fluid.

16. The device of claim 14, wherein the at least one of the reservoirs reservoir contains a nonaqueous fluid.

17. The device of claim 16, wherein the nonaqueous fluid comprises an organic solvent.

18. The device of claim 14, wherein the fluid contains a biomolecule.

19. The device of claim 14, wherein the fluid is at least partially frozen.

20. The device of claim 1, wherein at least one reservoir contains a substance capable of existing as a fluid at a temperature of about 0° C. to about 100° C.

21. The device of claim 1, further comprising a means for altering the relative position of the analyzer with respect to the plurality of reservoirs.

22. The device of claim 1, wherein the analyzer is positioned to receive acoustic radiation reflected from a free surface of a fluid contained in a reservoir.

23. The device of claim 1, wherein the analyzer is adapted to analyze a characteristic of acoustic radiation to determine the volume of fluid in each reservoir.

24. The device of claim 1, wherein the analyzer is adapted to analyze a characteristic of acoustic radiation to determine a property of the fluid in each reservoir.

25. The device of claim 24, wherein the property is height.

26. The device of claim 24, wherein the property is surface orientation.

27. The device of claim 1, wherein the acoustic generator represents a component of an acoustic ejector for ejecting droplets from the plurality of reservoirs.

28. The device of claim 27, further comprising a focusing means for focusing the acoustic radiation generated by the acoustic generator.

29. The device of claim 28, wherein the focusing means is adapted to focus the acoustic radiation according to the results of acoustic analysis performed by the analyzer.

30. The device of claim 1, further comprising a storage means for storing the results of acoustic analysis performed by the analyzer.

31. The device of claim 30, wherein the storage means comprises rewritable data storage media.

32. The device of claim 30, wherein the storage means comprises permanent data storage media.

33. The device of claim 30, further comprising the results of acoustic analysis performed by the analyzer stored in the storage means.

34. The device of claim 1, further comprising a temperature control means for controlling the temperature of the plurality of reservoirs.

35. A method for acoustically determining a property of the contents of one or more reservoirs, comprising the steps of:
    (a) selecting a reservoir from a plurality of reservoirs each comprising a solid surface, wherein a portion of each reservoir is adapted to contain a fluid;
    (b) positioning an acoustic radiation generator in acoustic coupling relationship to the selected reservoir;
    (c) actuating the acoustic radiation generator to generate acoustic radiation so that the generated acoustic radiation is then transmitted through the solid surface and through the portion of the selected reservoir adapted to contain a fluid to an analyzer capable of analyzing a characteristic of the transmitted radiation, the characteristic corresponding to a property of the contents of the selected reservoir; and (d) operating the analyzer to analyze the characteristic of the transmitted acoustic radiation.

36. The method of claim 35, further comprising repeating steps (b), (c), and (d) for the remaining reservoirs.

37. The method of claim 35, further comprising, after step (a), step (a') dispensing a quantity of fluid from the reservoir.

38. The method of claim 37, wherein step (a') is carried out through acoustic ejection.

39. The method of claim 37, wherein step (a') is carried out after sufficient time has passed to allow for the contents of the reservoir to melt.

40. The method of claim 35, wherein step (b) comprises positioning the acoustic radiation generator such that acoustic radiation generated by the acoustic generator is directed toward a free surface of a fluid within the reservoir.

41. The method of claim 35, further comprising, after step (d), step (e) correlating the characteristic to the volume of the contents in the reservoir.

42. The method of claim 35, further comprising, after step (d), step (e) correlating the characteristic to a property of the contents in the reservoir.

43. The method of claim 42, wherein the property is height.

44. The method of claim 42, wherein the property is surface orientation.

45. The method of claim 35, wherein step (d) comprises measuring the travel time of the transmitted acoustic radiation through the reservoir.

46. The method of claim 35, further comprising (e) storing the results of acoustic analysis performed by the acoustic analyzer.

47. The method of claim 35, wherein each of steps (a), (b), (c), and (d) is carried out while the reservoir is in a sealed state.

48. A method for accurately dispensing fluid from a reservoir, comprising the steps of:

(a) positioning an acoustic radiation generator in acoustic coupling relationship to a reservoir selected from a plurality of reservoirs, wherein a portion of each reservoir is adapted to contain a fluid;

(b) transmitting acoustic radiation generated by the acoustic radiation generator through at least the portion of the selected reservoir adapted to contain a fluid;

(c) analyzing a characteristic of the transmitted acoustic radiation; and (d) dispensing fluid from the selected reservoir according to the analysis of the characteristic of the transmitted acoustic radiation.

49. The method of claim 48, wherein step (d) is carried out through acoustic ejection.

50. The method of claim 48, wherein steps (a), (b), (c), and (d) are repeated for another reservoir selected from the plurality of reservoirs.

51. In a device for dispensing one or more fluids from a plurality of reservoirs each having a portion adapted to contain a fluid, the improvement comprises providing:

an acoustic radiation generator for generating acoustic radiation;

a means for positioning the acoustic radiation generator in acoustic coupling relationship to each reservoir such that acoustic radiation generated by the acoustic radiation generator is transmitted through at least the portion of each reservoir adapted to contain a fluid; and an analyzer for analyzing a characteristic of acoustic radiation.

52. The device of claim 51, wherein the acoustic radiation generator represents a component of an acoustic ejector.

* * * * *